United States Patent [19]

Sneider

[11] Patent Number: 4,605,404

[45] Date of Patent: Aug. 12, 1986

[54] DISPOSABLE PAD FOR PANTY HOSE

[76] Inventor: Vincent R. Sneider, 3422 Hallcrest Dr., Hampton Hall, Atlanta, Ga. 30319

[21] Appl. No.: 691,845

[22] Filed: Jan. 16, 1985

[51] Int. Cl.$^4$ .............................................. A61F 13/16
[52] U.S. Cl. .................. 604/385 R; 604/389
[58] Field of Search ................................. 604/385–402

[56] References Cited

U.S. PATENT DOCUMENTS

| | | | |
|---|---|---|---|
| 84,703 | 12/1868 | Moore | 604/394 |
| 2,043,325 | 6/1936 | Jackson | 604/401 |
| 2,047,054 | 7/1936 | Beyer, Jr. | 604/385 R |
| 2,591,079 | 4/1952 | Leaton | 604/386 |
| 2,852,026 | 9/1958 | Karr | 604/385 R |
| 4,023,570 | 5/1977 | Chinai et al. | 604/390 |
| 4,230,113 | 10/1980 | Mehta | 604/385 R |

Primary Examiner—C. Fred Rosenbaum
Assistant Examiner—S. Vinyard
Attorney, Agent, or Firm—Ralph R. Roberts

[57] ABSTRACT

There are shown two configurations of a disposable pad particularly for panty hose. Each pad is secured by a self-stick adhesive (three strips shown) to the inner surface of the crotch of the panty hose. This pad is made with an impervious backing sheet to which a pair of fill members is secured as by localized areas of heat-welding, laser-welding and the like. Preferably, these fill members are treated to provide indicators and are abutted at the longitudinal midpoint of the pads. A release sheet is furnished to protect the self-stick adhesive until time of use. The release sheet, the backing sheet and fill members are die-cut and provide exterior edges whereat the fill portions are exposed to provide a soft surface to the user. Four notches are formed in the edge portions of the pad to assist in placement and attachment of the pad to the undergarment. These notches assist in bending the pad and also provide straddling of seams produced in the sewing of the panty hose as a complete garment.

17 Claims, 6 Drawing Figures

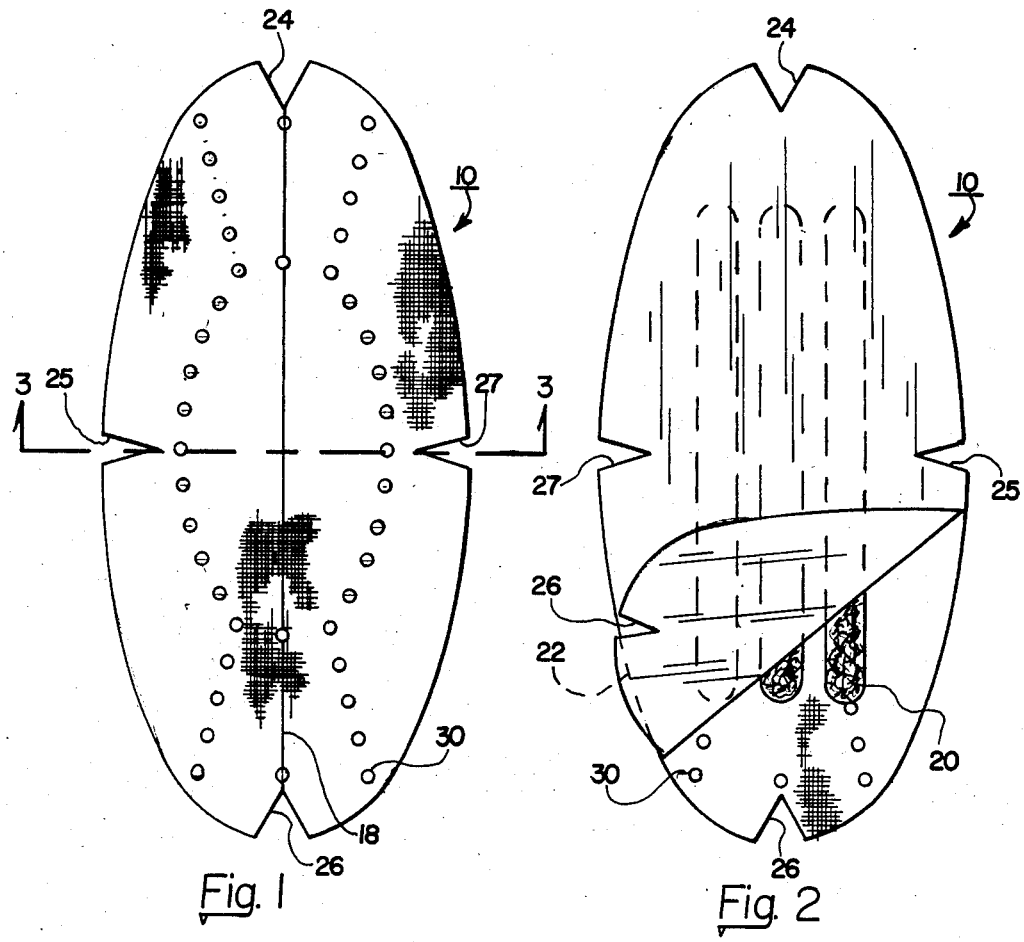
Fig. 1
Fig. 2
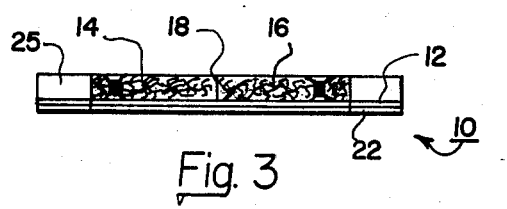
Fig. 3

DISPOSABLE PAD FOR PANTY HOSE

BACKGROUND OF THE INVENTION

1. Field of the Invention

With reference to the classification of art as established in and by the United States Patent Office, this invention is believed to be found in the general class identified as "Surgery" (Class 604) and in the subclasses therein pertaining to means and methods for collecting body fluids or waste material, and particularly for a catamenial receptacle, and more particularly for pads secured in a worn undergarment and secured in place by adhesive means.

2. Description of the Prior Art

Panty pads retained by adhesive means in the undergarment of a woman user have been known and used for at least fifteen years. There have been many patents drawn to this concept and these removable pads are now used in the several millions yearly and worldwide. The manufacture and distribution is under many trademark names and contours. These pads, as far as is known, are made in many thicknesses and absorbency capabilities. Some pads are designed for use between menstrual periods and some are for these periods. Some also include deodorant and/or bacteria inhibitors. Panty hose having seam assembly procedures present placement and retention problems. The pads available before this invention were for insertion and use in panties in which the crotch area is usually devoid of seams. Adhesive securing in such undergarments presents little or no problem, but with panty hose the construction thereof presents a securing problem. The present invention overcomes such problems and provides a comfortable disposable pad.

SUMMARY OF THE INVENTION

This invention may be summarized, at least in part, with reference to its objects. It is an object of this invention to provide, and it does provide, a disposable pad for use in and with panty hose. This pad has localized interior securing of the pad fill to an impervious backing member of thin plastic and with the edges of the pad open to provide a soft, exposed exterior portion to the user of the pad.

It is a further object of this invention to provide, and it does provide, a pad in which the outer peripheral extent remains unenclosed or bound and in which there are formed four outer notches disposed at about ninety degrees from each other and providing therewith means for adjusting to the seams of manufacture of the panty hose.

In brief, there are two shapes or contours of the disposable pad of this invention. In a first configuration, an ovoid shape is presented, and in the second configuration an hour-glass shape is utilized. In both pads, the fill is selected for its absorbency and with or without a top cover is attached to an impervious backing at localized portions interior of the outer periphery so as to present exterior portions as soft portions of fill material. A releaseable sheet portion of substantially the same configuration as the pad is provided to retain integrity of a plurality of strips of release adhesive which is provided and exposed so as to retain the pad in the desired position.

Whether ovoid or hour-glass in configuration, the pad is formed with four notches that provide assistance in placing and retaining the pad in the desired position. The fill of and for the pad has a dividsion or separation at substantially the midportion of the pad fill. This division is lengthwise of the pad so that preferably one-half provides indicator means for such as a sugar indicator for diabetics and the remaining or other half of the fill is treated to have indicating properties for ovulation discharge. Such treating of the fill produces no known irritation and with new developments is quite inexpensive.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen two specific embodiments of a disposable pad for panty hose as adopted for use with the crotch portion thereof and showing a preferred means for construction of said pad. These specific embodiments have been chosen for the purposes of illustration and description as shown in the accompanying drawings wherein:

BRIEF DESCRITPION OF THE DRAWINGS

FIG. 1 represents a plan or top view of an ovoid-shaped pad as provided and used in a panty hose garment;

FIG. 2 represents a back or rear view of the pad of FIG. 1 and showing a release sheet partially removed, exposing strips of adhesive utilized to retain said pad in place;

FIG. 3 represents a sectional view taken on the line 3—3 of FIG. 1 and looking in the direction of the arrows;

Figure 4:
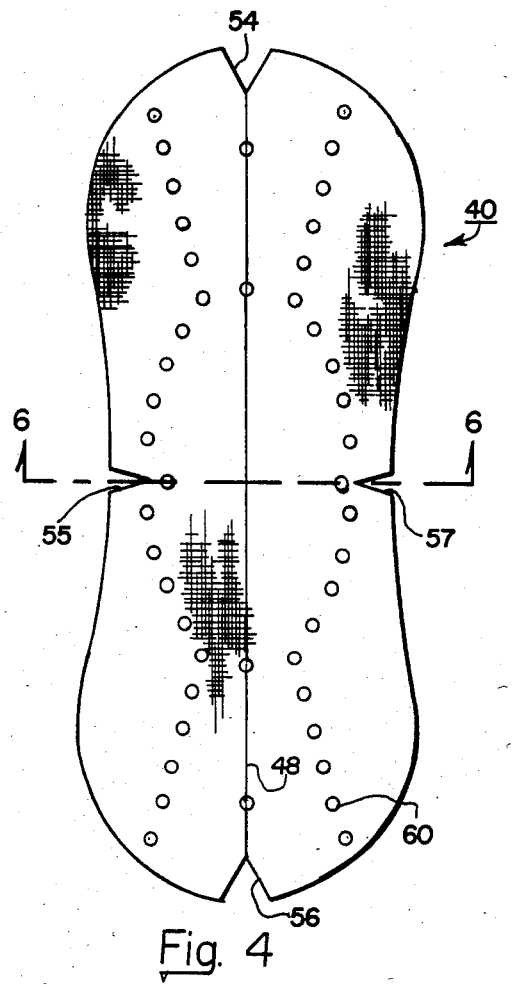
FIG. 4 represents a plan or top view of an hour-glass shaped pad as provided and used in a panty hose garment.

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIGS. 1, 2 AND 3

Referring next to the drawings, there is depicted a thin pad, generally identified as 10, and having a generally ovoid shape. This pad in the drawings is shown substantially full scale. An improved panty pad particularly for use with panty hose is depicted and utilized with an impervious backing sheet 12 which is usually of thin plastic sheeting. To this backing sheet 12 is secured a fill member which is anticipated to be of two treated materials. A left portion 14 abuts a fill member 16 at about a centerline 18. These fill members 14 and 16 may or may not have a top porous cover member. The left and right fill portions are separately treated to indicate separate indicators. For example, one portion may be treated to provide a diabetic positive indicator, and the other fill member may be treated to indicate ovulation or lack of ovulation.

Backing sheet 12 has its exterior surface locally coated with three strips of releasable adhesive 20, as is commonly used with self-stick panty pads which have been available and used for at least ten years. To protect this adhesive against unwanted contact and contamination, there is provided a release sheet 22 which may be of waxed paper, coated plastic or the like. As seen in FIG. 1, this pad is formed with notches 24, 25, 26 and 27. These notches enable the pad to be mounted in a panty hose garment. In the construction of panty hose, there are seams by which the various parts are sewn together. Notches 24 and 26 are disposed to straddle the front-to-back seam and notches 25 and 27 are disposed to straddle a sideway seam. If there are no sideway seams, these notches 25 and 27 assist in the bowing of the pad in use.

The fill members 14 and 16 may be of any conventional structure, from loose-type material to pressed-together fill. The fill is anticipated to have a high-absorbency capability. It is to be noted that where and when a top cover member is used, such a cover is very porous so as not to impede the passing therethrough of discharge fluids. The fill is secured to the impervious backing sheet by local securing means such as laser welds, heat seals and the like. These securing means are small areas or localized as depicted. These securing spots are identified as 30 and are arrayed in a selected pattern. The edge portions of this pad are open and not secured by an edge seam or adhesive so that the edges are exposed and soft and do not chafe the skin of the user.

USE AND OPERATION OF PAD OF FIGS. 1 THROUGH 3

The pad 10 is removed from its package wrapper, not shown, and as a single pad the release sheet 22 is removed by manipulation. With the removal of the release sheet 22, the adhesive strips 20 are exposed and are utilized to position and retain the pad 10 in the crotch of the panty hose. The seams of manufacture are used as guides for the desired positioning of the pad. After a desired period of use, the pad is removed and the treated fill is then examined, if desired, to ascertain whether the user has excess sugar or has ovulation fluids in her discharge.

EMBODIMENT OF FIGS. 4, 5 AND 6

Figure 5:
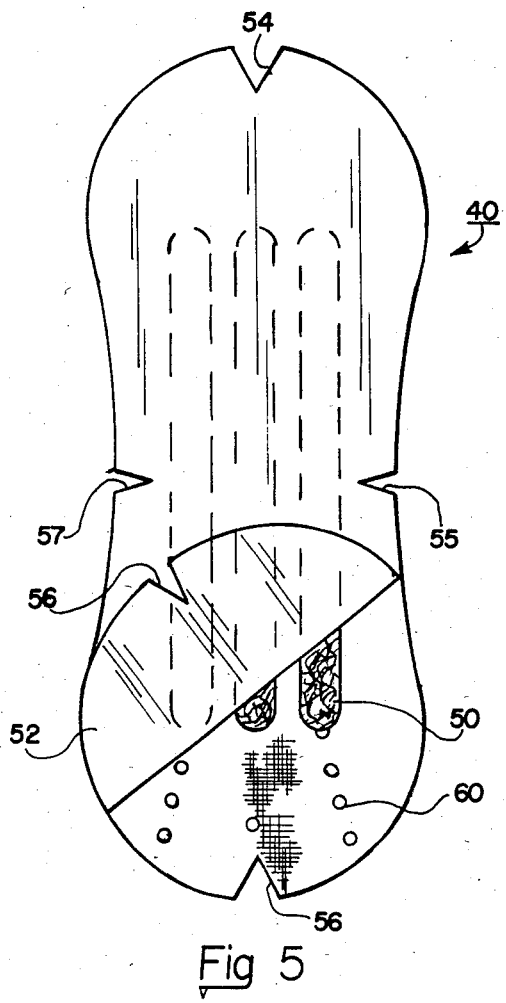
FIG. 5 represents a back or rear view of the pad of FIG. 4 and showing a release sheet partially removed, exposing strips of adhesive utilized to retain said pad in place.
Figure 6:
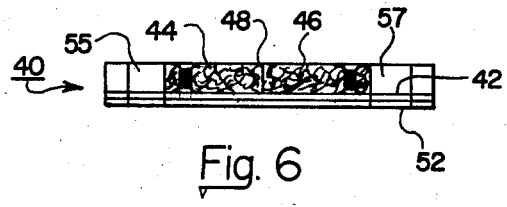
FIG. 6 represents a sectional view taken on the line 6—6 of FIG. 4 and looking in the direction of the arrows.

In the pad of FIGS. 4, 5 and 6, a thin pad, as in FIGS. 1-3, is anticipated to be provided and is similar but for the shape or configuration. In FIGS. 4, 5 and 6, the pad is generally identified as 40 and has a generally hour-glass configuration. A backing sheet 42 is configured with a like shape and is impervious to fluids. Fill-member portions 44 and 46 abut each other at substantially a longitudinally centerline 48. As in the other pad, a porous top cover may or may not be utilized. The left and right fill portions, as in the prior-identified pad, may be or are treated to provide the desired indicators.

As in the other pad, the backing sheet 42 is depicted with three strips of releasable adhesive 50, as is commonly used with self-stick panty pads. A release sheet 52 is provided and, as the pad contour is die-cut, this release sheet is also contour cut. A plurality of notches 54, 55, 56 and 57 are formed in the peripheral outside of the pad and, as above, are disposed to accommodate seams in the panty hose. The fill members 44 and 46 are secured to the backing sheet 42 by local securing means such as laser welds, heat seals and the like. These securing spots are identified as 60 and are arrayed in selected pattern sufficient to retain the fill to the said backing sheet 42. As in the prior-described pad, the edge portion is open or exposed so that the fluff or fill is not secured by an edge seam or adhesive so that such edges do not chafe the skin of the user.

USE AND OPERATION OF PAD OF FIGS. 4, 5 AND 6

As in the pad of FIGS. 1-3, this pad 40 is removed from a package wrapper, not shown, and as a single pad 40 has the release sheet 42 removed by manipulation, exposing the adhesive strips 50. The user then positions and places the adhesive strip portions to the panty and crotch portion of the panty hose. The seams in the panty hose may be used as guides for positioning and use of the pad. After the desired period of use, the pad is removed and discarded. If examination is desired or required, the staining of the pad and fluid flow are observed.

The pads above depicted show both an ovoid and hour-glass configuration, but this configuration may be changed if desired. The pad for panty hose is formed with die-cut edge or exterior portions so that the soft absorbent fill provides the contacting surfaces with the user's skin. In both pads, the self-stick adhesive is shown in three strips, but the adhesive may be applied as small dots, patterned areas or other designs known to the trade. The pattern of adhesive is not significant except that the release sheet have a portion that is easily manipulated for removal of the release sheet from the adhesive when time for use. The notches enable the pad to be placed and pressed into position in the panty portion of the panty hose.

The thickness of the pad is a matter of selection and absorbency requirement. It is to be noted that a longitudinal cut or separation is provided in each pad. This separation insures that bending longitudinally is achieved without difficulty. The notches assist in the bending and placing of the pad in position in the crotch of undergarment of the user. The treating of the fill to provide indicators is now quite reasonable and fill so treated, as far as is known, does not have side effects. Such treatment to provide indications provides an automatic indicator and that a problem does or does not exist.

The above-described disposable pad provides a basis for a method of construction that is believed to be novel. The construction of this pad includes the steps of:

(a) providing an impervious backing-sheet member and contouring said backing-sheet member so as to conform to the desired shape of the pad;

(b) applying self-stick adhesive in defined patterns on the outer or backside of the backing-sheet member, with said applied adhesive so disposed as to leave a portion or portions of said backing-sheet member absent self-stick adhesive;

(c) arraying a pair of fill members and carrying said fill members in close proximity to said backing sheet, said fill members arranged so as to abut each other and establish a longitudinal division or line substantially at a longitudinal midpoint of said pad;

(d) locally securing the fill members to the impervious sheet so that each securing means is disposed interior of the outer edges of the pad;

(e) providing a release sheet and covering all of the self-stick adhesive portions by and with said release sheet, the release sheet so disposed as to leave a portion of said backing sheet absent contact with said self-stick adhesive;

(f) forming a contour of the pad including the backing-sheet member, the fill members and the release sheet so that the edges of the pad are exposed and these exposed portions of the soft fill are disposed to contact the skin of the user, and (g) forming at least two notches in the outer-edge portions of the pad, said notches disposed so as to assist in straddling a seam or seams formed in the construction of the panty hose.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the posotion in which the disposable pad for panty hose may be constructed or used.

While two particular embodiments of the pad and construction have been shown and described, it is to be understood that the invention is not limited thereto and protection is sought to the broadest extent the prior art allows.

What is claimed is:

1. A disposable pad for attachment to panty hose and like undergarments, said pad secured by a self-stick adhesive affixed to an outer surface of said pad, this pad including:
   (a) an impervious backing-sheet member, said backing sheet contoured to conform to the desired shape of the pad;
   (b) self-stick adhesive portions applied to the outer or backside of the backing-sheet member, said applied adhesive so disposed as to leave a portion or portions of said backing-sheet member absent self-stick adhesive;
   (c) a plurality of absorbent fill portions of equal size carried by and in close proximity to said backing sheet, said fill portions being of substantially the same thickness and arranged so as to abut each other, thereby providing a substantially equal division of the absorbent fill portions of said pad;
   (d) a multiplicity of localized securing means, each disposed interior of the outer edges of the pad, said securing means affixing the fill members to the impervious backing-sheet member;
   (e) a release sheet covering all the self-stick adhesive portions on the backside of the impervious backing-sheet member, said applied adhesive and release sheet so disposed as to leave a portion of said backing sheet absent contact with said self-stick adhesive;
   (f) the periphery of said pad including the backing-sheet member, the absorbent fill portions and the release sheet being formed such that the edges of the absorbent fill are disposed to contact the skin of the user, and
   (g) at least two notches formed in the outer-edge portions of the pad, said notches disposed so as to straddle any formed seam or seams in the panty hose or like undergarment to which said pad is to be attached in use.

2. A disposable pad, as in claim 1, in which the self-stick adhesive portions are three strips spaced and applied longitudinally and terminating at less than the edges of the pad.

3. A disposable pad, as in claim 1, in which the notches are four in number and are disposed about ninety degrees from each other.

4. A disposable pad, as in claim 3, in which the pad configuration is generally ovoid.

5. A disposable pad, as in claim 3, in which the pad configuration is generally an hour-glass.

6. A disposable pad, as in claim 1, in which the pad fill includes treatment before assembly and with said treatment providing indicator means from a co-mingling with the discharge.

7. A disposable pad, as in claim 6, in which the treated pad fill has one fill portion treated to indicate a diabetic condition and the other fill portion treated to indicate ovulation or absence thereof.

8. A disposable pad, as in claim 1, in which the localized securing means is provided by laser welds.

9. A disposable pad, as in claim 1, in which the localized securing means is by heat-sealing.

10. A disposable pad, as in claim 1, in which the self-stick adhesive portions are small dots arrayed in a random pattern.

11. A method of forming and constructing a disposable pad for attachment to panty hose and like undergarments which is secured by a self-stick adhesive applied to an outer surface member of said pad, the method including the steps of:
   (a) providing an impervious backing-sheet member and contouring said backing-sheet member so as to conform to the desired shape of the pad;
   (b) applying self-stick adhesive in defined patterns on the outer or backside of the backing-sheet member, with said applied adhesive so disposed as to leave a portion or portions of said backing-sheet member absent self-stick adhesive;
   (c) arranging a plurality of absorbent fill portions and carrying said absorbent portions in close proximity to said backing sheet, said portions being of substantially the same thickness and positioned so as to abut each other, thereby providing a substantially equal division of the absorbent fill portions of said pad;
   (d) locally securing the absorbent fill portions to the impervious sheet so that each securing means is disposed interior of the outer edges of the pad;
   (e) providing a release sheet and covering all of the self-stick adhesive portions by and with said release sheet, the release sheet so disposed as to leave a portion of said backing sheet absent contact with said self-stick adhesive;
   (f) trimming the exterior periphery of the pad including the backing-sheet member, the absorbent fill portions and the release sheet so that the edges of the pad are exposed and these exposed portions of the absorbent fill are disposed to contact the skin of the user, and
   (g) at least two notches formed in the outer-edge portions of the pad, said notches disposed so as to straddle any formed seam or seams in the panty hose or like undergarment to which said pad is to be attched in use.

12. A method of forming a disposable pad, as in claim 11, which includes the further step of applying the self-stick adhesive in three strips spaced and applied longitudinally and with these strips terminating at least than the edges of the pad.

13. A method of forming a disposable pad, as in claim 11 in which the forming of the notches includes forming four notches in the periphery of the pad.

14. A method of forming a disposable pad, as in claim 11, which includes the further step of treating the fill before assembly, with said treatment providing indicator means from a comingling with the discharge.

15. A method of forming a disposable pad, as in claim 14, in which the treated pad fill has one fill portion treated to indicate a diabetic condition and the other fill portion treated to indicate ovulation or absence thereof.

16. A method of forming a disposable pad, as in claim 11, in which the locally securing means is provided by laser welds.

17. A method of forming a disposable pad, as in claim 11, in which the locally securing means is provided by heat-sealing.

* * * * *